US006432392B1

(12) United States Patent
Ashcroft et al.

(10) Patent No.: US 6,432,392 B1
(45) Date of Patent: Aug. 13, 2002

(54) ANTIPERSPIRANT SALTS, AND METHODS OF THEIR PREPARATION

(75) Inventors: Alexander Thomas Ashcroft; Philippa Margaret Smith, both of Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/579,099

(22) Filed: May 25, 2000

(30) Foreign Application Priority Data

May 25, 1999 (GB) ............................... 9912167

(51) Int. Cl.[7] .............................. A61K 7/32; A61K 7/38; A61K 7/00; C01B 7/00; C01F 7/48
(52) U.S. Cl. ........................ 424/68; 423/462; 423/495; 424/65; 424/401
(58) Field of Search ............................ 424/401, 65, 68; 423/462, 495

(56) References Cited

U.S. PATENT DOCUMENTS 2,876,163 A * 3/1959 Garizio et al. ................ 167/90
4,359,456 A 11/1982 Gosling et al.

FOREIGN PATENT DOCUMENTS

| DE | 2117094 A | * 11/1971 |
| EP | 0337464 | 10/1989 |
| EP | 0976387 | 3/2000 |

OTHER PUBLICATIONS

International Search Report Application No. PCT EP 00/04207 mailed Sep. 12, 2000.

* cited by examiner

Primary Examiner—Jose' G. Dees
Assistant Examiner—Marina Lamm
(74) Attorney, Agent, or Firm—Kevin J. Stein

(57) ABSTRACT

An antiperspirant active salt made by treating an aluminum salt of general formula;

$$Al_2(OH)_{6-a}X_a$$

wherein X is Cl, Br or I, and a is 0.3 to 4.0, with an effective amount of a phosphorus containing material, and ageing the salt.

4 Claims, No Drawings

ANTIPERSPIRANT SALTS, AND METHODS OF THEIR PREPARATION

This invention relates to novel basic aluminium antiperspirant salts having improved properties, and to methods of their preparation.

Many conventional forms of antiperspirant active salt are aluminium chlorhydrates (ACH), and have the general formula $Al_2(OH)_{6-a}X_a$, where X is a halogen and preferably chlorine, and a is between about 0.5 and 5. Such salts have generally been used in topical antiperspirant products for many years, and have found widespread consumer acceptance.

It is known to attempt to increase the efficacy of such active salts by a number of routes. A popular route has been to vary the processing parameters used in the production of the salt, to attempt to modify the polymer form of the salt, and hence to affect amongst other things the salt's efficacy in topical antiperspirant compositions.

A further route for modification of such salts is to modify them chemically. An example of this approach is to be found in EP 337,464, in which a solution of basic aluminium chloride is modified by the addition to it of a predetermined amount of monosilicic acid. Such treatment is said to result in an increase in efficacy of the basic aluminium chloride. However, the synthetic routes described in this application are complicated, and as such may not be straightforward to commercialise or carry out on a large scale.

In general, whilst activated aluminium chlorhydrate (AACH) compounds made by prior methods have produced antiperspirant actives which have a generally relatively high efficacy in topical products, it is desirable that antiperspirant actives continue to be made of a relatively high efficacy, certainly compared to aluminium chlorhydrate, whilst being made at the same time as cheaply as possible. In particular, many of the processes which are known for making AACHs utilise heating regimes which last for many hours, for example for 24 hours or more, and may require temperatures in excess of 100° C. Clearly such heating regimes require much energy, and are therefore expensive, and may cause the resulting salts to be expensive to produce.

We have surprisingly found after much investigation that it is possible to provide novel antiperspirant actives from conventional aluminium chlorhydrate antiperspirant salts by treating them with an effective amount of a phosphorus containing compound. The resulting salts have good antiperspirant efficacy compared with conventional unmodified aluminium chlorhydrate salts, and further it is possible to manufacture such salts at relatively low temperatures, thus providing activated aluminium chlorhydrate salts by means of an energetically less demanding, and consequently cheaper process.

Thus, according to a first aspect of the invention, there is provided an antiperspirant salt made by treating an aluminium salt of general formula:

$$Al_2(OH)_{6-a}X_a$$

wherein X is Cl, Br or I, and a is 0.3 to 4, preferably 0.6 to 4.0, with an effective amount of a phosphorus containing material, and ageing the salt.

According to a further aspect of the invention, there is provided a method of improving the antiperspirant efficacy of an aluminium compound having the empirical formula:

$$Al_2(OH)_{6-a}X_a$$

wherein X is Cl, Br or I, and a is between 0.3 and 4.0, preferably 0.6 to 4.0, comprising treating a solution (preferably an aqueous solution) of the aluminium compound with an effective amount of a phosphorus containing compound, and ageing the resultant solution.

According to yet a further aspect of the invention, there is provided a method of manufacturing a modified aluminium chlorhydrate composition comprising treating a solution (preferably an aqueous solution) of an aluminium compound having the empirical formula:

$$Al_2(OH)_{6-a}X_a$$

wherein X is Cl, Br or I, and a is between 0.3 and 4.0, preferably 0.6 to 4.0, with an effective amount of a phosphorus containing compound, and ageing the resultant solution.

The conditions under which the reaction may be carried out are not critical, but may conveniently be carried out by dissolving an aqueous solution of a phosphorus containing material, such as dilute phosphoric acid, in a solution of aluminium chlorhydrate. Ageing may conveniently be carried out at room temperature, but may also be carried out either at elevated or reduced temperatures (in the latter case should it be necessary to cool the reaction mixture).

With regard to the resulting product, it is preferred that the resulting aluminium salt has an Al/X ratio of between 1.5:1 and 2.5:1, and that the aluminium concentration in the solution resulting after treatment with the phosphorus source is between 0.1 and 10 wt %, more preferably 0.5 and 5.0 wt %, and even more preferably 1.0–4.0 wt %. In a highly preferred embodiment, the resultant solution is dried to provide a salt which has a water content of less than 12 wt %.

In aspects of the invention involving a solution of a phosphorus containing material, the phosphorus concentration in the resultant aged solution is preferably in the region 0.01 to 10 wt %, more preferably 0.5 to 8 wt %, more preferably 1 to 5 wt % , even more preferably 1.0 to 4.0% by weight.

In all aspects of the invention, it is preferred that the concentration of any sulphate and/or sulphuric acid present is less than 0.05 mole per mole of aluminium present. It is also preferred that the molar concentration of such sulphur containing materials is less than half the molar concentration of phosphorus containing compounds present. More preferably, such sulphur containing materials are not present.

In this specification, reference to aluminium and phosphorus concentrations refer to the concentrations of any aluminium or phosphorus containing species present; examples of the former including aluminium chlorhydrate and examples of the latter including phosphoric acid.

The combination of parameters described herein has been found to result in an activated salt which is preferred, and which provides a good level of antiperspirant efficacy when incorporated into a topical antiperspirant composition, in particular when compared to unmodified aluminium chlorhydrate.

Preferably, the anion in the polymeric aluminium compound is chloride. Conveniently, a may be between 0.8 and 2.1; preferably a is between 0.8 and 1.5, and most preferably is about 1.0.

Preferably, the ratio of Al/X in the final product is in the region 1.6:1 to 2.3:1, and is conveniently in the region 1.7:1 to 2.0:1.

Conveniently, solutions of salts made according to the invention can be left for periods of 2 hours to thirty days to age. Ageing need not be carried out at elevated temperatures, and indeed can be carried out at room temperature.

Conveniently, the water content in the resulting (dried) antiperspirant active salt is no lower than about 2%, is preferably at least about 4%, is more preferably at least 6%, and is even more preferably at least 8% by weight of the composition. Preferably, the water content of the salt is less than 12%, more preferably less than 10% by weight of the salt. It has been found that reducing the water content of the salt is desirable for the long term stability of the salt. With regard to the minimum water content, it is believed that whilst too little water is in itself not harmful to the stability of the salt, the drying regimes to which the salt needs to be subjected to get the water content to particularly low levels may be deleterious to the more active polymer species in the salt. Water content may conveniently be measured using a moisture balance, for example a Sartorius MA30 moisture balance, used on an "auto" programme with a set point of 100° C.

Dried activated aluminium actives according to the invention can conveniently be isolated on an industrial scale by freeze drying or spray drying. Freeze drying is generally considered to be a less harsh drying technique, and hence may be considered to be a preferred drying method in certain circumstances, though spray drying may be considered to be a preferred technique in other circumstances, since it tends to result in a dried salt with a more consistent and desirable particle size distribution. This may therefore negate the need for further processing to provide the desired particle size distribution. Where spray drying is used as the drying method, it is preferred that the dried powder be cooled as soon as possible after the drying step, for example by conveying it from the drying stage to the next stage (e.g. a storage stage) in a cooled, low humidity current of air.

Compositions which utilise aluminium salts produced according to the invention may be any of the topically applied forms, including sticks, roll-on lotions, aerosols, creams and soft solids, and pump spray formulations. It is highly preferable that such compositions comprise a carrier material for the aluminium salt. The carrier material may be hydrophobic or hydrophilic, solid or liquid. Preferred carrier materials are liquids. Hydrophobic liquids suitable for use with the chelator salts of the invention include liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, and aliphatic or aromatic ester oils (eg. isopropyl myristate, lauryl myristate, isopropyl palmitate, diisopropyl sebecate, diisopropyl adipate, or C8 to C18 alkyl benzoates). The amount of carrier material employed is preferably from 30% to 99%, more preferably 60% to 98%, expressed as a weight percentage of the total weight of all the components of the composition, excluding any propellants present.

Certain compositions according to the invention, notably those that take the form of sticks, creams, or soft solids, preferably contain a structurant. Such materials, when employed, are preferably present at from 1% to 30% by weight of the composition. Suitable structurants for use in compositions of the invention include cellulosic thickeners, such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate.

The topical compositions according to the invention are preferably anhydrous; that is, the composition vehicle (i.e. the components of the composition, excluding the antiperspirant active salt itself) contain less than about 2%, more preferably less than 1% by weight of water. It is also preferred that topical compositions deliver the antiperspirant active as a suspended solid, and not as a solution, though topical compositions containing antiperspirant active solutions are also contemplated.

Although not limited as such, the compositions formed according to the invention may have particular utility in propellant driven aerosol compositions, in which zirconium based actives, currently the most efficacious available, are prohibited in some countries. Topical compositions containing actives formed according to the invention may be formulated using those cosmetic ingredients that are used in the formulation of the particular topical composition, depending on the product form.

Conveniently, actives formed by the process according to the invention have a relatively high proportion of polymers contained in Band III compared to those in Band II of the Standard Basic Aluminium Chloride Solution Size Exclusion Chromatogram of the Size Exclusion Chromatography Test, as described in U.S. Pat. No. 4,359,456, the content of which is incorporated herein by reference. Preferably, the ratio of Band III to Band II material is greater than about 1:1. Conveniently the level of Band III material is more than about 30% by weight of the aluminium polymer species, more preferably greater than about 40% by weight.

Characterisation of materials containing species differing in size by means of size exclusion chromatography (SEC) is generally known. The method of size exclusion chromatographic procedures used for the characterisation of the basic aluminium compounds of this invention is as outlined below, and is used for characterisation on the basis of the percentage of aluminium in species less than 100 Angstroms in size.

The analytical procedure used to determine the percentage of aluminium in species having a size less than 100 Angstroms (i.e. material in Bands I, II, III, and IV) was performed using a stainless steel column of dimensions 30 cm long and 7.0 mm internal diameter. This was packed with spherical porous silica of nominal particle size 5 micrometers diameter, an average pore size of 50 Angstroms diameter, a pore volume of 0.8 cc/g and a surface area of 450 $m^2/g$. A suitable silica was that available commercially as Nucleosil 50 from Macherey-Nagel GmbH.

Although the columns used in the actual method employed by the Applicants were obtained ready packed from Jones Chromatography Limited of Hengoed, Mid-Glamorgan, Wales, if it were necessary to pack a column with the silica it could conveniently be carried out by the high-pressure slurry method (see "Silica Gel and Bonded Phases, Their Production, Properties and Use in LC", by R P W Scott, Published by John Wiley and Sons, 1993, page 60) using hexane as the packing medium. In all cases the column would be equipped at the bottom with a zero dead volume fitting containing a 2 micrometer porosity stainless steel support and after packing would be capped with another zero dead volume fitting containing a 2 micrometer stainless steel frit.

The packed column was connected into a chromatographic system consisting of an automatic sampler, high-pressure pump, column, and a differential refractive index detector to monitor sample fractions as they were eluted. The refractive index detector was linked to an integrator to provide a real-time chromatogram and a data system that was programmed to calculate the relative chromatographic band areas of the fractions as a function of their elution times. The system was instructed to measure the areas of bands not resolved to the baseline by dropping perpendiculars from the lowest point of the valleys separating the bands to the baseline.

Newly packed columns were eluted with 200 ml of methanol at a flow rate of about 10 ml/minute, using a high pressure pump, to consolidate the bed and wash out the packing medium. This was followed by a change of eluent to the medium to be used for the analytical separations, in this case an aqueous solution containing 0.1 molar sodium nitrate and 0.01 molar nitric acid, and elution continued at a rate of 0.5 ml/minute until a flat base-line was achieved.

To provide a sample for conditioning the column and to act as a calibration standard a Standard Basic Aluminium Chloride Solution was prepared. This was carried out by dissolving 52.1 g of aluminium powder (99.97% aluminium by weight, grade 20/D supplied by The Aluminium Powder Company Limited of Holyhead, Anglesey, North Wales) in a solution of 93.2 g of aluminium chloride hexahydrate (supplied by Sigma-Aldrich Company Limited of Gillingham, Dorset SP8 4XT, UK) in 354.7 g of deionized water at about 90° C. in a stirred vessel equipped with a reflux condenser. When all of the aluminium had dissolved the solution was filtered to remove traces of insoluble impurities and allowed to cool to room temperature. This gave a Standard Basic Aluminium Chloride Solution that contained 12.5% aluminium by weight.

The column was conditioned by the application of multiple injections of 10 microlitre samples of the Standard Basic Aluminium Chloride Solution, diluted to 2.5% aluminium by weight, until a constant chromatogram was obtained from successive injections.

To prepare test solutions of materials for analysis for their Band I, II, III, and IV contents, those already in solution were used undiluted unless the aluminium concentration exceeded 2.5% by weight aluminium, in which case they were diluted with deionized water to provide a solution containing 2.5% by weight aluminium. Solid materials were dissolved in deionized water to give solutions containing 2.5% by weight aluminium. These solutions were treated in an ultrasonic bath for two minutes then filtered through 0.2 micrometer porosity cellulose acetate filter units. The preparation of the test solutions was carried out within 10 minutes of their application to the column. Sample solutions were applied to the top of the column as 1 microlitre injections and eluted at a rate of 0.5 ml/minute.

When a sample of Standard Basic Aluminium Chloride Solution was diluted to 2.5% aluminium by weight and applied to the column four main bands were obtained. They were characterised by means of the ratio of the retention times of the principal peak in each band to the retention time of the peak due to the totally included species (in the case of basic aluminium chlorides the totally included species arise from the presence of hydrochloric acid. This can be shown by comparison of its retention time with that of a sample of 0.01 molar hydrochloric acid.) and their chromatographic band areas expressed as percentages of the total chromatographic band area representing aluminium-containing material:

|  | Band I | Band II | Band III | Band IV |
|---|---|---|---|---|
| Relative retention time (minutes) | 0.66 | 0.75 | 0.81 | 0.94 |
| Band area (% of total aluminium band area) | 26.1 | 61.3 | 8.4 | 4.2 |

Comparison of the total aluminium content of the eluted fractions representing Bands I to IV with that of another sample of the same volume that had not passed through the column showed that there was complete elution of aluminium species from the column. In a further experiment it was found that the relative aluminium contents of the separated fractions, expressed as percentages of the total aluminium contents of Bands I to IV, agreed closely with the relative area percents determined by integration of the signals from the refractive index detector for the same bands.

It will be appreciated by those skilled in the art that mechanisms of separation other than the principal mechanism of size exclusion may play a part in this type of chromatography. Examples of the processes would be adsorption effects and hydrodynamic effects. Thus although it is possible for a given column and constant operating conditions to lead to invariable relative retention times, minor variations in particle size range and pore size distribution of the packing materials may lead to slight differences in relative retention times and the splitting of the main bands. In our experience with standard columns packed with different batches of the specified packing material, the four aluminium-containing bands consistently fall within the ranges indicated:

|  | Band I | Band II | Band III | Band IV |
|---|---|---|---|---|
| Relative retention time (minutes) | 0.56–0.72 | 0.73–0.79 | 0.80–0.87 | 0.88–0.98 |

Quantitatively, the amount of aluminium in the various Bands expressed as a percentage of the total aluminium of the compound under test is given by:

$$\% \text{ Aluminium Bands I, II, III, or IV} = \frac{\text{Area of band corresponding to Band I, II, III, or IV fraction}}{\text{Sum of the areas of the bands corresponding to Bands I, II, III, and IV}}$$

In accordance with a further aspect of the invention there is provided a topical antiperspirant or deodorant composition comprising an effective amount of a basic aluminium salt prepared in accordance with the process described above.

An advantage of aluminium active salts according to the invention is that they can be made according to processes which do not involve heating for excessive periods, and indeed can be made at room temperature, yet they have efficacies which are in excess of conventional unmodified ACH salts.

The invention will now be further illustrated by way of the following examples.

Experimental

A 50% by weight aluminium chlorhydrate solution was prepared by dissolving 8 g of aluminium chlorhydrate (Aloxicoll PF40, ex. BK Giulini Chemie) in 8 ml de-mineralised water. This solution was added slowly to 56 ml of stirred 0.42 M and 0.21 M solutions of phosphoric acid. The solutions were left for 4 days to age. The resulting clear solutions were frozen and freeze dried to a powder, and were analysed by SEC.

The SEC chromatograms showed an increase in Band III material, especially for the lower concentration phosphoric acid solution, and also a reduction in the level of Band II material, compared to the chromatograms for aluminium chlorohydate, which is indicative of high antiperspirant efficacy.

Further experiments carried out using a similar experimental method to that above indicate that preferred compositions derive from aged solutions comprising in the region of 0.5–8%, more preferably 1–3% by weight phosphorus. They also indicated that compositions which contain amounts of phosphorus have superior levels of efficacy when used in topical antiperspirant compositions compared to compositions containing unmodified aluminium chlorhydrate, and indeed may have similar levels of efficacy to activated aluminium chlorhydrate (AACH), which is often made by thermal processing of aluminium chlorhydrate.

To this end, solutions containing 2% by weight of phosphorus were prepared as described above and dried to give phosphoric acid treated ACH and AACH salts. These salts were then incorporated into topical roll on lotion compositions at the same levels (wt %) as control samples prepared from conventional, untreated ACH and AACH salts. The compositions were tested in a hot room to determine their antiperspirant efficacy, and sweat rate reduction results were obtained for each composition. The method used for evaluating efficacy was that described in U.S. Pat. No. 4,359,456, Test method II (col. 11), except that the panel consisted of at least 30 women who had not used antiperspirant for 17 days before the test; also, in terms of the analysis of data, the % reduction was not calculated for each day separately, and significance was not calculated by applying Duncans Multiple Range Test.

The results indicated that the phosphoric acid treated compositions, having average antiperspirant efficacies of 35% for the ACH sample and 32% for the AACH sample, had similar levels of antiperspirant efficacy to conventional AACH (32%), and superior efficacy to unmodified ACH (25%).

FORMULATION EXAMPLES

Composition 1

Antiperspirant salts prepared according to the invention may be incorporated into suspension aerosol products of the following composition using conventional processing methods.

| Component | Amount (wt %) | Function |
|---|---|---|
| Antiperspirant salt | 5.0 | Active |
| Volatile silicone[1] | 10.0 | Carrier/emollient |
| Talc | 1.0 | Tactile properties |
| Clay[2] | 0.75 | Suspending agent |
| Fragrance | 0.75 | |
| Hydrocarbon | to 100 | Propellant |

[1]D5 (cyclopentasiloxane) grade, eg. DC 245 Fluid.
[2]Bentone 38V, ex Rheox.

Composition 2

Antiperspirant salts prepared according to the invention may be incorporated into concentrated aerosol products of the following composition using conventional processing methods.

| Component | Amount (wt %) | Function |
|---|---|---|
| Antiperspirant salt | 21.0 | Active |
| Bentone gel VS-5 PC[1] | 18.5 | Suspension/dispersion |
| Volatile silicone[2] | 10.2 | Carrier/emollient |
| Dimethicone | 8.5 | Carrier/emollient |
| Isopropyl myristate | 1.5 | Emollient |
| Fragrance | 0.3 | |
| Isobutane | 40 | Propellant |

[1]ex Rheox.
[2]D5 (cyclopentasiloxane) grade, eg. DC 245 Fluid.

Composition 3

Antiperspirant salts prepared according to the invention may be incorporated into suspension antiperspirant stick products of the following composition using conventional processing methods.

| Component | Amount (wt %) | Function |
|---|---|---|
| Volatile silicone[1] | 45.0 | Carrier/emollient |
| Antiperspirant salt | 20.0 | Active |
| Stearyl alcohol | 15.0 | Structurant |
| PPG-10 cetyl alcohol | 5.0 | Surfactant |
| Hydrogenated castor oil | 5.0 | Structurant |
| Phenyl trimethicone | 5.0 | Emollient |
| PPG-15 stearyl ether | 5.0 | Surfactant |

[1]DC 345 Fluid, ex Dow Corning.

Composition 4

Antiperspirant salts prepared according to the invention may be incorporated into soft solid/dry cream products of the following composition using conventional processing methods.

| Component | Amount (wt %) | Function |
|---|---|---|
| Volatile silicone[1] | 65.0 | Carrier/emollient |
| Antiperspirant salt | 24.0 | Active |
| C18–36 acid triglyceride/tribehenin | 6.5 | Structurant |
| Dimethicone | 4 | Carrier/emollient |
| Fragrance | 0.5 | |

[1]D5 (cyclopentasiloxane) grade, eg. DC 245 Fluid.

What is claimed is:

1. A method of improving the antiperspirant efficacy of an aluminum compound having the empirical formula:

$$Al_2(OH)_{6-a}X_a$$

wherein X is Cl, Br or I, and a is 0.3 to 4.0, comprising treating a solution of the aluminium compound with an effective amount of an acidic water soluble source of phosphorus, and ageing the resultant solution, to gain a salt with good antiperspirant efficacy.

2. A method of manufacturing a modified aluminium chlorhydrate composition comprising treating a solution of an aluminium compound having the empirical formula:

$$Al_2(OH)_{6-a}X_a$$

wherein X is Cl, Br or I, and a is between 0.3 and 4.0, with an effective amount of an acidic water soluble source of phosphorus, and ageing the resultant solution, to gain a salt with good antiperspirant efficacy.

3. A method according to claim 1, wherein the resultant solution is an aqueous solution.

4. A method according to claim 1, wherein the concentration of any sulphate and/or sulphuric acid present is less than 0.05 mole per mole of aluminium present.

* * * * *